United States Patent
Wu et al.

(10) Patent No.: US 12,011,377 B2
(45) Date of Patent: Jun. 18, 2024

(54) MEDICAL DEVICE WITH IMPROVED COATING

(71) Applicant: PICOSUN OY, Espoo (FI)

(72) Inventors: Xiaopeng Wu, Helsinki (FI); Juhana Kostamo, Vantaa (FI); Niku Oksala, Tampere (FI); Riina Ritasalo, Espoo (FI)

(73) Assignee: PICOSUN OY, Espoo (FI)

( * ) Notice: Subject to any disclaimer, the term of this patent is extended or adjusted under 35 U.S.C. 154(b) by 278 days.

(21) Appl. No.: 16/832,715

(22) Filed: Mar. 27, 2020

(65) Prior Publication Data

US 2020/0306063 A1  Oct. 1, 2020

Related U.S. Application Data

(60) Provisional application No. 62/826,338, filed on Mar. 29, 2019.

(51) Int. Cl.
*A61F 2/82* (2013.01)
*C23C 16/455* (2006.01)

(52) U.S. Cl.
CPC ........ *A61F 2/82* (2013.01); *A61F 2210/0076* (2013.01); *A61F 2250/003* (2013.01); *A61F 2250/0067* (2013.01); *A61F 2310/00604* (2013.01); *A61F 2310/00616* (2013.01); *C23C 16/45525* (2013.01)

(58) Field of Classification Search
CPC ........ A61F 2210/0076; A61F 2250/003; A61F 2250/0035; A61F 2250/0067–0068
See application file for complete search history.

(56) References Cited

U.S. PATENT DOCUMENTS

| 2003/0083646 | A1 * | 5/2003 | Sirhan | A61F 2/91 |
| | | | | 623/1.42 |
| 2008/0082162 | A1 * | 4/2008 | Boismier | A61L 31/022 |
| | | | | 623/1.38 |
| 2009/0186068 | A1 | 7/2009 | Miller et al. | |
| 2018/0015209 | A1 * | 1/2018 | Johnson | A61L 29/106 |

FOREIGN PATENT DOCUMENTS

FR   2927815 A1 *  8/2009 ............. A61L 31/10

OTHER PUBLICATIONS

Machine translation of FR 2927781 A1. 28 pages. Accessed Jun. 6, 2023. (Year: 2023).*
Wang et al., "ALD mediated heparin grafting on nitinol for self-expanded carotid stents", Colloids and Surfaces B: Biointerfaces, 2016, pp. 390-398, vol. 143, No. 1.
Zhong et al., "Atomic layer deposition enhanced grafting of phosphorylcholine on stainless steel for intravascular stents", Colloids and Surfaces B: Biointerfaces, 2014, pp. 238-247, vol. 121, No. 1.

* cited by examiner

*Primary Examiner* — Rebecca S Preston
(74) *Attorney, Agent, or Firm* — NIXON & VANDERHYE

(57) ABSTRACT

A medical device is provided comprising an at least one surface deposited with at least a first conformal coating and a second conformal coating deposited on the first conformal coating, wherein the first conformal coating comprises the first chemical substance and the second conformal coating comprises the second chemical substance. In some instances, the first coating is deposited over the first chemical substance and the second coating is deposited over the second chemical substance.

8 Claims, 1 Drawing Sheet

On outer surface

| 30 2$^{nd}$ coating+Substance B |
| 20 1$^{st}$ coating+Substance A |
| 10 Surface |

On inner and outer surface

| 30 2$^{nd}$ coating+Substance B |
| 20 1$^{st}$ coating+Substance A |
| 10 Surface |
| 20 1$^{st}$ coating+Substance A |
| 30 2$^{nd}$ coating+Substance B |

MEDICAL DEVICE WITH IMPROVED COATING

FIELD OF THE INVENTION

The present invention generally relates to chemical deposition methods for coating joints implants, coated articles and uses.

BACKGROUND OF THE INVENTION

This section illustrates useful background information without admission of any technique described herein representative of the state of the art.

Once a stent is placed in position, into a coronary artery, for example, a common problem that may occur is a blockage of the stent caused by the body's healing response. The blockage can be partial or total, and it can be sudden or proceed gradually. To facilitate the healing process of the body and to prevent possible intimal hyperplasia and thrombus formation, the stent can be smeared with drug powder that prevents excessive growth of endothelium and formation of thrombus. However, the smeared drug is only present on a top surface of the stent and normally it will be lost very quickly due to dissolution of drug powder when brought into contact with bodily fluids.

A common problem with cardiovascular and other stents (gastrointestinal, urological) is endothelial i.e. intimal (cardiovascular stents) or epithelial (gastrointestinal, urological) hyperplasia and subsequent occlusion of the treated area. In cardiovascular stents, another problem is thrombus formation and occlusion of the stent, which is typically acute. Since treatment of an occluded or a stenosed area with stent usually requires balloon dilatation, there is considerable injury and subsequent inflammation in the treated area, further complicated with elastic recoil and restenosis. A stent inserted to counteract recoil not only mechanically maintains the flow, but also contains a slowly eluting drug (drug eluting stents) to counteract late restenosis due to hyperplasia and, in case of arteries, thrombosis.

First generation of antiproliferative drugs include paclitaxel and sirolimus, which were followed by everolimus, zotarolimus, umirolimus, novolimus, and amphilimus, which have different degree of lipophilicity, bioavailability, half-life, anti-inflammatory activity, effect on re-endothelialisation, effect on smooth muscle cells, affinity and efficacy against hyperplasia. Due to these differences, it is likely that the ultimate stent product should contain a combination of these drugs releasable at different phases (early inflammation, late hyperplasia and thrombosis and neoatherosclerosis).

Until present, drug release from stents has been controlled via coating the surfaces with different polymers and by utilizing different biodegradable stent platforms. The challenge with these solutions is that application of drugs and polymers controlling their release should not impair mechanical characteristics of the stent. By avoiding utilization of polymers, inflammatory responses can be reduced. Polymer-free stents range from those with smooth surface, those with micro- or macroporous or even nanoporous surfaces, and ultimately drug-filled stents or stents coated with the drug.

Wang et al [1] discloses use of ALD technology to deposit a layer (10 nm) of aluminium oxide ($Al_2O_3$) on Nitinol surface as an intermediate functional layer. ALD has been used for surface functionalization.

Zhong et al [2] pertains to a study of ALD-deposited $Al_2O_3$ layer for adhesion and integrity of drug-carrying polymer coating. Publication does not provided for dissolving layer(s) and drug releasing component(s).

Patent application publication US 2009/0186068 (Miller et al) discloses provision of nanophase single- or multiple layer time release coatings over drugs attached to metal surfaces. The coatings are deposited by atomic plasma deposition (APD). In publication, porosity (a nanoroughened surface) and a layer thickness define the drug release, wherein a titanium oxide- or an alumina oxide surface has a thickness that releases the biomolecule over selected period of time. Publication does not concern provision of implantable devices, such as stents.

SUMMARY OF THE INVENTION

An objective of the present invention is to solve or to at least alleviate each of the problems arising from the limitations and disadvantages of the related art. The objective is achieved by various embodiments of a medical device comprising conformal coatings configured for controlled release of chemical substances into biological fluids (bodily fluids) and/or biological tissues. Thereby, in an aspect of the invention a medical device is provided.

In embodiment, a medical device is provided comprising at least one surface deposited with at least a first conformal coating and a second conformal coating deposited on said first conformal coating, wherein the first conformal coating comprises a first chemical substance and the second conformal coating comprises a second chemical substance.

In another embodiment, a medical device is provided comprising at least one surface deposited with at least a first conformal coating and a second conformal coating, wherein the first conformal coating is deposited over a first chemical substance disposed on said at least one surface of said medical device, and wherein the second conformal coating is deposited over the second chemical substance disposed on the first conformal coating.

In embodiment, the first chemical substance comprises a pharmaceutically active compound, and wherein the second chemical substance comprises a component modulating the action of the pharmaceutically active compound provided with the first chemical substance.

In embodiment, said second chemical substance is configured to catalyze degradation and/or to inhibit or potentiate the action of the pharmaceutically active compound provided with the first chemical substance.

In embodiment, the medical device is an implantable medical device. In embodiment, the medical device is a stent.

In embodiment, the first and second conformal coatings are deposited on a predetermined surface or surfaces of the medical device. In embodiment, the first and second conformal coatings are deposited on external and/or internal surfaces of said medical device.

In embodiment, said first and second coatings are configured to dissolve in biological fluids at different rate.

In embodiment, at least one of the first and second coatings are deposited with Atomic Layer Deposition (ALD). In embodiment, at least one of the first and second coatings are deposited with Plasma Enhanced Atomic Layer Deposition (PEALD).

Without limiting the scope and interpretation of the patent claims, certain technical effects of one or more of the example embodiments disclosed herein are listed in the following:

Controlled drug(s) release from an implantable device, such as stent;

Prolonged drug delivery time to prevent certain undesired effects, such as intimal hyperplasia and formation of thrombus and therefore occlusion and/or infection;

Two-phase drug release with different rates inside the body to suit better for different phases of healing;

Increased sterility management e.g. due antimicrobial or antibacterial drugs and/or coatings;

ALD is thin film, therefore, dissolving amounts are extremely small;

ALD thickness control and dissolving rates of metal oxides, such as ZnO and $Al_2O_3$, for example, as well as metal nitrides and oxynitrides, can provide well-controlled drug release, for years, if needed;

Several ALD materials are biocompatible, and can provide a safe solution.

In the present disclosure, materials with a layer thickness below 1 micrometer (μm) are referred to as "thin films".

The expression "a number of" refers herein to any positive integer starting from one (1), e.g. to one, two, or three; whereas the expression "a plurality of" refers herein to any positive integer starting from two (2), e.g. to two, three, or four.

The terms "first" and "second" are not intended to denote any order, quantity, or importance, but rather are used to merely distinguish one element from another.

BRIEF DESCRIPTION OF THE DRAWINGS

The invention will now be described, by way of example only, with reference to the accompanying drawings, in which.

DETAILED DESCRIPTION

The invention pertains to provision of a medical device comprising a number of conformal coatings configured for controlled release of an at least one chemical substance into biological fluids and/or tissues.

Figure 1:
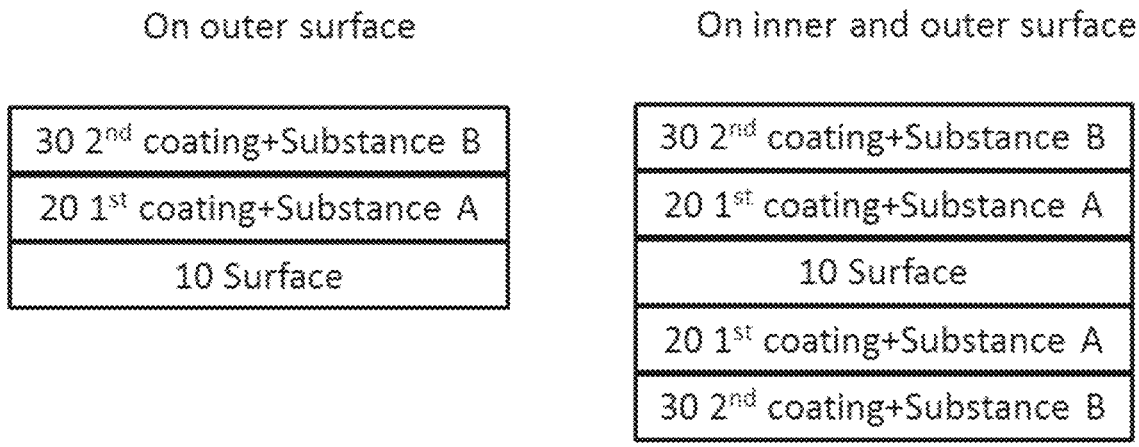
FIGS. 1 and 2 schematically illustrate a surface structure of a medical device, according to different embodiments.

FIG. 1 shows a medical device with a surface structure according to an embodiment. The device comprises a substrate with at least one surface 10, deposited with a first conformal coating 20 and a second conformal coating 30 deposited on said first conformal coating.

Figure 2:
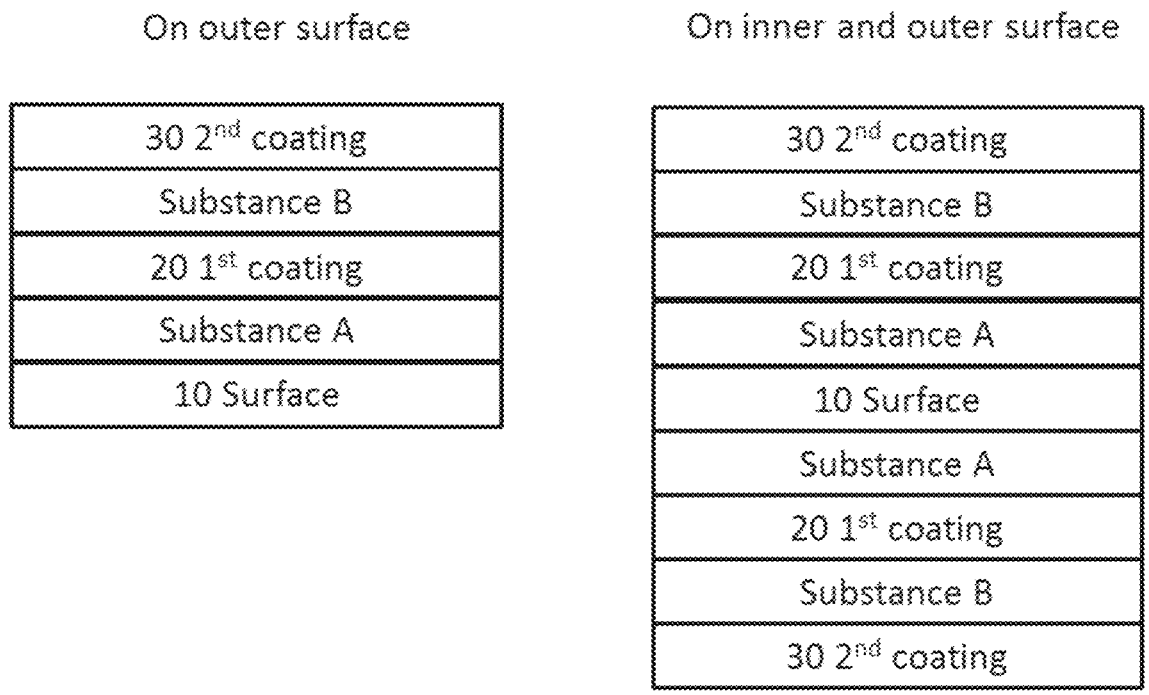

The substrate may be configured as an essentially planar substrate with a first and second surfaces (e.g. top- and bottom). Alternatively, the substrate may be configured as an item having an internal volume; therefore the first- and second surfaces of such substrate shall be referred to as an inner- and outer surfaces, for example. FIGS. 1 and 2 illustrate the latter configuration.

In configuration shown on FIG. 1, the first conformal coating 20 comprises a first chemical substance A and the second conformal coating comprises a second chemical substance B. In configuration of FIG. 1, the chemical substances A and B are embedded into the material of the 1$^{st}$ and 2$^{nd}$ coating layers, accordingly.

FIG. 2 shows a medical device with a surface structure according to another embodiment. The device comprises a substrate with at least one surface 10 deposited with the first conformal coating 20 and the second conformal coating 30. Said first conformal coating 20 is, in turn, deposited over the first chemical substance (Substance A) disposed on said at least one surface 10 of said medical device, and the second conformal coating 30 is deposited over the second chemical substance (Substance B) disposed on the first conformal coating 20.

It should be appreciated that more coating layers can be applied on the top of each other to create a complex stack structure.

In configuration shown on FIG. 1, the coating layers 20, 30, act as carriers for the substances A and B; whereas in embodiment shown on FIG. 2 the coating layers 20, 30 coat mentioned substances A and B, accordingly.

FIGS. 1 and 2 thus illustrate exemplary configurations having a coating layer stack on one surface of the substrate/the device (marked as "on outer surface", left side) and the same on both surfaces of the substrate (marked as "on inner and outer surface", right side).

In embodiments, at least one of the mentioned conformal coatings are deposited with Atomic Layer Deposition (ALD). In some configurations, it is preferred that at least one of the first- and second coatings are deposited with Plasma Enhanced Atomic Layer Deposition (PEALD).

The basics of an ALD growth mechanism are known to a skilled person. ALD is a special chemical deposition method based on the sequential introduction of at least two reactive precursor species to at least one substrate. It is to be understood, however, that one of these reactive precursors can be substituted by energy when using, for example, photon-enhanced ALD or plasma-assisted ALD, for example PEALD, leading to single precursor ALD processes. For example, deposition of a pure element, such as metal, requires only one precursor. Binary compounds, such as oxides can be created with one precursor chemical when the precursor chemical contains both of the elements of the binary material to be deposited. Thin films grown by ALD are dense, pinhole free and have uniform thickness. In some instances, Chemical Vapour Deposition (CVD) may be utilized.

The benefit of using PEALD in the present invention is that by virtue of PEALD the deposition temperature can be significantly decreased, even down to about 20 deg C., as compared to significantly higher temperatures, such as about 100 deg C. and above, required for many conventional (thermal) ALD processes.

The at least one substrate is typically exposed to temporally separated precursor pulses in a reaction vessel to deposit material on the substrate surfaces by sequential self-saturating surface reactions. In the context of this application, the term ALD comprises all applicable ALD based techniques and any equivalent or closely related technologies, such as, for example the following ALD sub-types: MLD (Molecular Layer Deposition), plasma-assisted ALD, for example PEALD (Plasma Enhanced Atomic Layer Deposition) and photon-enhanced Atomic Layer Deposition (known also as photo-ALD or flash enhanced ALD). The process can also be an etching process, one example of which being an ALE process. It should be noted that with PEALD and photon-enhanced ALD, the additive treatment can be limited to the surfaces visible to the radiation source.

ALD is based on alternating self-saturative surface reactions, wherein different reactants (precursors) provided as chemical compounds or elements in a nonreactive (inert) gaseous carrier are sequentially pulsed into a reaction space accommodating a substrate. Deposition of a reactant is followed by purging the substrate by inert gas. Conventional ALD deposition cycle proceeds in two half-reactions (pulse A—purge A; pulse B—purge B), whereby a layer of material is formed in a self-limiting (self-saturating) manner, typically being 0.05-0.2 nm thick. Typical substrate exposure time for each precursor ranges within 0.01-1 seconds.

Pulse A comprises a first precursor in a gaseous phase (first precursor vapor) and pulse B comprises a second precursor in a gaseous phase (second precursor vapor). Inactive gas and a vacuum pump are typically used for purging gaseous reaction by-products and the residual reactant molecules from the reaction space during purge A and purge B. A deposition sequence comprises at least one deposition cycle. Deposition cycles are repeated until the deposition sequence has produced a thin film or coating of desired thickness. Deposition cycles can also be either simpler or more complex. For example, the cycles can include three or more reactant vapor pulses separated by purging steps, or certain purge steps can be omitted. On the other hand, photo-enhanced ALD has a variety of options, such as only one active precursor, with various options for purging. All these deposition cycles form a timed deposition sequence that is controlled by a logic unit or a microprocessor.

With reference back to FIGS. 1 and 2, the first chemical substance comprises a first pharmaceutically active compound, and the second chemical substance comprises a second pharmaceutically active compound. The chemical substance can further comprise a combination of pharmaceutically active compounds provided in a suitable carrier. In embodiments, the first chemical substance can be configured as drug A, for example; whereas the second chemical substance can be configured as drug B, accordingly. By a pharmaceutically active compound, we refer to a chemical- and/or biological compound or complex of compounds possessing essentially therapeutic activity aiming at treating and/or preventing a disease and/or serving to maintain health of a patient.

In some configurations, the first chemical substance comprises the pharmaceutically active compound (e.g. drug A) and the second chemical substance comprises a component B modulating the action of the pharmaceutically active compound A provided with the first chemical substance. The component B can be configured to catalyze the degradation of the compound A, to inhibit- or to promote the action of said compound A, or to potentiate the effect of the compound A. Any other modulating activity can be conceived. The modulator component B can be configured as a pharmaceutically active compound (drug B). Described combination allows for altering the properties of the (ALD)-deposited coating to enable regulation of drug-related activities, such as release, action and/or neutralization, with high precision.

In configurations, the second chemical substance is thus configured to catalyze degradation and/or to inhibit or potentiate the action of the pharmaceutically active compound provided with the first chemical substance.

The medical device is advantageously configured as an implantable medical device. In some instances, the medical device is configured as a stent or any type of three-dimensional tubular medical device suitable for inserting/implanting into a patient body. The medical device, such as a stent or a 3D tubular device, is configured for controlled drug(s) release in the body, optionally, for a prolonged time period. The stent can be configured as a drug-eluting stent. In some instances, the medical device, such as a tube or a stent, is configured for prolonged drug release.

The first and the second conformal coatings are thus deposited on a predetermined surface or surfaces of the medical device. In some instances, said first and the second conformal coatings are deposited on external and/or internal surfaces of said medical device, accordingly.

The first coating 20 and the second coating 30 are preferably configured to dissolve in biological fluid(s), such as blood, for example, internal organs and/or biological tissues with different rate. The coating(s) can be rendered dissolvable in said biological fluids optionally when surrounded with biological tissue by virtue of their composition.

Thus, any one of the first- and second conformal coatings can be provided as aluminium oxide ($Al_2O_3$), zinc oxide (ZnO), or a combination thereof. Selected ALD materials, such as $Al_2O_3$ and ZnO, are biocompatible. Said materials dissolve in controllable manner when in contact with the bodily fluids.

Additionally or alternatively, the first- and second coatings 20, 30 can be obtained, in non-limiting manner, with any one of titanium oxide ($TiO_2$), magnesium oxide (MgO), calcium oxide (CaO), or silicon dioxide/silica ($SiO_2$), which can be utilized alone or in combination.

Additionally or alternatively, the first and second coatings 20, 30 can be obtained with nitride and/or oxynitride, compounds, including, but not limited titanium-, aluminium- or silicon nitrides (TiN, AlN and SiN, accordingly) and their oxynitrides or a combination thereof.

While metal oxide species are the most effectively deposited by conventional ALD methods (thermal ALD) at generally lower temperatures (within a range of about 60-200 deg C., preferably, 80-120 deg C. depending on precursors and required quality), deposition of nitride- and oxynitride compounds may require utilizing plasma-assisted ALD methods, such as PEALD.

In some instances, the coating layers 20, 30 can be provided as laminate films containing more than one material (layer). For example, ALD or PEALD coatings 20, 30 on the surface(s) 10 can be implemented by sequentially directing first- and second precursors into the reaction space, wherein said precursors are allowed to react with each other to produce a deposition (sub)layer. A coating film of desired thickness (comprising a desired number of deposition (sub) layers) is formed in a number of deposition cycles. The coating film may comprise a number of such deposition (sub)layers, wherein each subsequent (sub)layer is "stacked" on the top of a preceding (sub)layer. A laminate can be produced with alternative e.g. Al oxide and Ti oxide material layers within the coating layer 20 or 30.

Utilization of any other appropriate material is not excluded.

In exemplary configuration, the first coating is provided as aluminium oxide ($Al_2O_3$).

The following configurations can be provided:
A) Tube/stent smeared with drug powder A
B) Tube/stent coating with material 1 (20)
C) Tube/stent smeared with drug powder B
D) Tube/stent coating with material 2 (30)
E) Controlled drug B release from coating material 2 (30) inside body in phase 1
F) Controlled drug A release from coating material 1 (20) inside body in phase 2
G) Prolonged drug release in body due different phases Materials 1 and 2 can be the provided as oxide, nitride- and/or oxynitride compound species disclosed hereinabove.

By using the ALD technology, it is possible to shield the drug powder with a layer that dissolves in a controlled manner when placed into contact with bodily fluids. Such dissolving barrier layer can be $Al_2O_3$ or $SiO_2$, for instance.

ALD is a conventionally conformal process and allows for controlling layer material thicknesses at angstrom level. Abovementioned Al- and Si oxides dissolve in a controlled manner when brought into contact with bodily fluids. By controlling thickness of the coating films 20, 30 deposited from $Al_2O_3$ and/or $SiO_2$, a dissolution time of said film and subsequent drug release can be controlled with high precision. Release time may be extended by embedding the medicine (A, B) in the ALD layer (wherein the medicine becomes distributed in the ALD layer, through the depth of the coating film 20, 30; FIG. 1). Additionally or alternatively, the drug release time can be controlled by modifying composition of the coating layer(s).

Two- or more phase systems can be provided (FIG. 2). In a manner described above, a differently dissolving ALD coating material can be selected for another phase (the second coating layer 30) and with another drug. By controlling the thickness of the second coating 30 and knowing its' dissolution rate, the second shielded drug can be released to the body in a controlled manner and in a different phase. In embodiment, the second coating is provided as zinc oxide (ZnO) having much slower dissolution rate as compared to $Al_2O_3$. Still, any other substance mentioned above can be utilized alone or in combination.

The topmost drug can be an antibacterial or antimicrobial substance to avoid infection, while the underlying (layer) drug can be the actual drug to facilitate healing processes in the body, optionally for a prolonged time.

The following configurations can be further provided:

The dug A possesses a predetermined therapeutic action and the drug B modulates dissolution rate and/or activity of said drug A.

The drug A is configured to facilitate the body healing process for prolonged time.

The drug B can be antibacterial or antimicrobial to avoid sudden infections when the medical device (the stent) is placed inside the body. The drug B can be also a compound that inhibits excessive growth of intima, i.e. occurring in intimal hyperplasia.

The drugs A and B can be present in different phases (shielded/coated by the $1^{st}$ and $2^{nd}$ coating layers 20, 30, respectively; FIG. 2) or they can be simultaneously provided directly in the coating layers 20, 30 (FIG. 1). In a latter case, different amounts of said drugs A, B can be provided to differentiate the phases.

It is preferred that dissolving rate for each ALD coating layer is adjusted beforehand.

In some configurations, each coating layer 20, 30 can comprise at least two different materials. In some other configurations, each said coating layer 20, 30 can comprise one material with specific thickness control in order to enable two different drug release phases.

In an aspect, use of the medical device according to the embodiments described above is provided for controlled drug release.

In embodiments, the selected ALD processes for drug shielding operate at low temperatures, such as for $Al_2O_3$ and ZnO deposition processes. Deposition temperatures for certain processes, such as $Al_2O_3$ from trimethylaluminium (TMA) and $H_2O$, are provided within a range between room temperature (20 deg C.) up to 300 deg C. and above. Other chemicals, such as $SiO_2$ can be deposited at the temperature range between 60 deg C. (and above) and about 300 deg C. (and above), where the use of PEALD will help to decrease the deposition temperature, as plasma can provide part of the reaction energy.

It shall be appreciated by those skilled in the art that the embodiments set forth in the present disclosure may be adapted and combined as desired. The disclosure is thus intended to encompass any possible modifications of the device and the related method, recognizable by those of ordinary skill in the art, within a scope of appended claims.

REFERENCES

1. Wang et al. ALD mediated heparin grafting on nitinol for self-expanded carotid stents. Colloids and Surfaces B: Biointerfaces. 2016, Vol. 143(1), pp. 390-398.
2. Zhong et al. Atomic layer deposition enhanced grafting of phosphorylcholine on stainless steel for intravascular stents. Colloids and Surfaces B: Biointerfaces. 2014, Vol. 121(1), pp. 238-247.

The invention claimed is:

1. A medical device comprising:
   At least one surface deposited with a at least a first conformal coating (comprising: a first chemical substance/pharmaceutically active compound embedded in a first material) and a second conformal coating (comprising: a second chemical substance/modulator component embedded into a second material) deposited on the at least a first conformal coating; wherein the second chemical substance/modulator component BOTH is configured to catalyze the degradation (i.e. initiate or increase the rate of chemical reaction) of AND potentiate the action (i.e. increase/intensify the effectiveness) of the first chemical substance/pharmaceutically active compound.

2. The medical device of claim 1, wherein the medical device is an implantable medical device.

3. The medical device of claim 1, wherein the medical device is configured as a stent.

4. The medical device of claim 1, wherein the at least one surface of the medical device on which the at least first and second conformal coatings are deposited includes a predetermined surface or surfaces of the medical device.

5. The medical device of claim 1, wherein the at least one surface of the medical device on which the at least first and second conformal coatings are deposited includes external and/or internal surfaces of said medical device.

6. The medical device of claim 1, wherein the at least first and second conformal coatings are configured to dissolve in biological fluids at different rates.

7. The medical device of claim 1, wherein at least one of the at least first and second conformal coatings is deposited with Atomic Layer Deposition (ALD).

8. The medical device of claim 7, wherein at least one of the at least first and second conformal coatings is deposited with Plasma Enhanced Atomic Layer Deposition (PEALD).

* * * * *